United States Patent [19]

O'Reilly et al.

[11] Patent Number: 4,912,221

[45] Date of Patent: Mar. 27, 1990

[54] CHIRAL 1,2,3,4-TETRAHYDROISOQUINOLINE-3-CARBOXYLIC ACID AND PRECURSORS AND PREPARATION THEREOF

[75] Inventors: Neil J. O'Reilly; Henry C. Lin, both of Grand Island, N.Y.

[73] Assignee: Occidental Chemical Corporation, Niagara Falls, N.Y.

[21] Appl. No.: 263,456

[22] Filed: Oct. 27, 1988

[51] Int. Cl.[4] .......................................... C07D 217/16
[52] U.S. Cl. ..................................... 546/147; 546/90; 549/441; 560/12; 560/17; 560/29; 560/33; 560/39; 560/41; 562/430; 562/442; 562/455
[58] Field of Search ................. 546/147, 90; 549/441; 560/12, 17, 29, 33, 39, 41; 562/430, 442, 455

[56] References Cited

U.S. PATENT DOCUMENTS 4,294,832  10/1981  Yoneda et al. ..................... 546/147
4,344,949  8/1982  Hoefle et al. ...................... 546/147

Primary Examiner—Richard L. Raymond
Assistant Examiner—James H. Turnipseed
Attorney, Agent, or Firm—James F. Tao; Arthur S. Cookfair

[57] ABSTRACT

The instant invention relates to optically pure, L-(S)forms of 1,2,3,4-tetrahydroisoquinoline-3-carboxylic acid compounds and their method of preparation from optionally pure L-phenylalanine precursor compounds and their preparation utilizing novel in situ cationic catalyst systems.

15 Claims, No Drawings

CHIRAL 1,2,3,4-TETRAHYDROISOQUINOLINE-3-CARBOXYLIC ACID AND PRECURSORS AND PREPARATION THEREOF

TECHNICAL FIELD

This invention is directed to optically pure, L-(S)-forms of 1,2,3,4-tetrahydroisoquinoline-3-carboxylic acid compounds and their method of preparation from optically pure L-phenylalanine precursor compounds and their preparation utilizing novel catalyst systems. The ultimately prepared compounds of the present invention are used as intermediates used in the preparation of substituted derivatives of 1,2,3,4-tetrahydroisoquinoline-3-carboxylic acid such as are described in U.S. Pat. No. 4,344,949 which display angiotensin-converting enzyme inhibitory activity.

BACKGROUND OF THE INVENTION

It is known that the L(S) configuration of certain 1,2,3,4-tetrahydroisoquinoline-3-carboxylic derivatives is required for improved biological activity for compounds possessing angiotensin-converting enzyme inhibitory activity as disclosed in U.S. Pat. No. 4,344,949. However, prior art synthesis techniques of chiral 1,2,3,4-tetrahydroisoquinoline-3-carboxylic acid intermediates have failed to produce compounds having acceptable levels of optical purity over 90% ee. The designation % ee (enantiomeric excess) represents: (% desired isomer—undesired isomer)/% total compound.

SUMMARY AND DETAILED DESCRIPTION OF THE INVENTION

The present invention relates to optically pure, i.e., L(S)-1,2,3,4-tetrahydroisoquinoline-3-carboxylic acid (IQCA), and to the method for its preparation. The optically pure L(S)-1,2,3,4-tetrahydroisoquinoline-3-carboxylic acid of the present invention is represented by the formula:

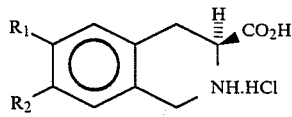

wherein $R_1$ and $R_2$ are independently hydrogen, lower alkyl, lower alkoxy, lower alkylthio, lower alkylsulfinyl, lower alkylsulfonyl, hydroxy or $R_1$ and $R_2$ together are methylenedioxy. When $R_1$ and/or $R_2$ are substituents containing a lower alkyl group, the preferred substituents are those of 1 to 4 carbon atoms. The preferred compound of the instant invention is L(S)-6,7-dimethoxy-1,2,3,4-tetrahydroixoquinoline-3-carboxylic acid.

The compounds of the instant invention are useful as intermediates in the production of substituted tetrahydroisoquinoline carboxylic acids such as quinapril which possess angiotensin-converting enzyme inhibiting activities which are disclosed in U.S. Pat. No. 4,344,949 to Hoefle et al which is hereby incorporated by reference.

The present invention also extends to optically pure intermediates which are utilized to prepare IQCA compounds of the present invention and the preparation thereof. These intermediates include L-phenylalanine derivatives of the formula:

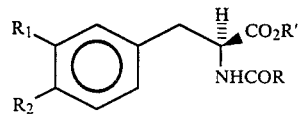

wherein R is $CH_3$— or $C_6H_5$—, R' is $CH_3$— or H— and $R_1$ and $R_2$ are defined above.

The following method is utilized for the preparation of the compound (II), the L-phenylalanine derivatives, of the instant invention.

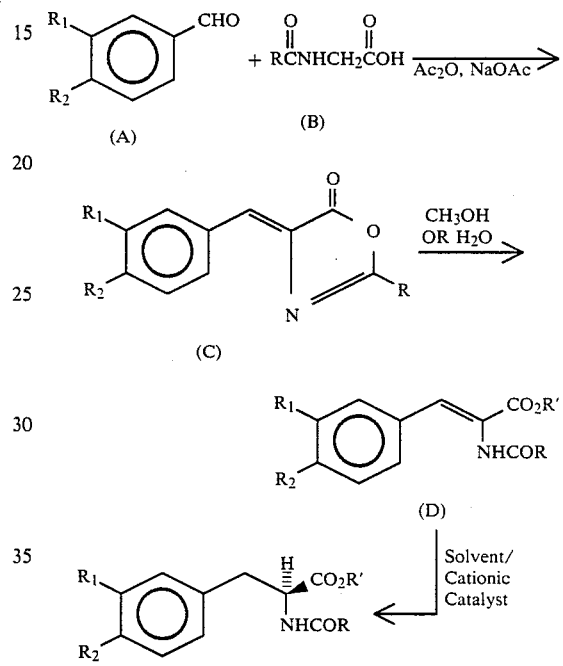

wherein R, R', $R_1$ and $R_2$ are defined above. The production of compound (D) analogs from its precursor compounds is well-known in the prior art and exemplified in Butterick et al Can. J. Chem. 52, p. 2873 (1974).

Optically pure L-phenylalanine derivatives of formula (II) are prepared from correspondingly R and R' substituted compounds of formula (D) by asymmetric hydrogenation utilizing a novel in situ cationic catalyst system. The hydrogenation reaction is otherwise carried out according to a conventional manner in a solvent such as methanol, tetrahydrofuran, ethanol, isopropanol, diethyl ether, dioxane or the like.

The in situ cationic catalyst system is comprised of a cationic bisdiene metal complex with a non-nucleophilic anion together with at least one chiral phosphine ligand.

The cationic bisdiene metal complex and non-nucleophilic anion are represented by the formula:

$$[M(Diene)_2]^+ X^- \qquad (E)$$

wherein M is selected from rhodium, platinum, ruthenium, palladium and nickel; Diene represents a suitable diene such as norbornadiene and cyclooctadiene; and $X^-$ is a non-nucleophilic anion selected from $PF_6^-$, $ClO_4^-$ and $BF_4^-$.

The chiral phosphine ligands (L) which are utilized in the instant invention are commercially available from Aldrich and include but are not limited to:

PROPHOS—((R)-(+)-1,2-bis (diphenylphosphino propane)

BINAP—((R)-(+)2,2'-bis (diphenylphosphino)-1,1'binaphthyl)

CHIRAPHOS—(2R, 3R)- or (2S, 3S)-(—)-bis(diphenylphosphino) butane

DIPAMP—(1R, 2R)- or (1S, 2S)-bis(phenyl-4-methoxyphenylphosphino)-ethane

NORPHOS—(2S, 3S)- or -(2R, 3R)-bis (diphenylphosphino) bicyclo- [2.2.1]-hepta-5-ene DIOP—(+) or (—) 2,3-O-isopropylidene-2, 3-dihydroxy-1, 4-bis (diphenylphosphino) butane CAMPHOS—(1S, 3R)- or (1R, 3S)-bis (diphenylphosphinomethyl)-1,2,3-trimethylcyclopentane DIOXOP—(2S, 4S)- or (2R, 4R)-bis(diphenylphosphinomethyl)-1,3-dioxolane.

These cationic bisdiene metal complex salts are prepared by mixing a neutral diene metal complex, such as [RhCl(norbornadiene)]$_2$, with an equivalent of a non-nucleophilic anion source, such as AgBF$_4$. After removing the silver chloride formed, by filtration, an equivalent of a diene, such as norbornadiene, is added. The chiral in situ cationic catalysts are then prepared in the hydrogenation flask by the addition, with the rigorous exclusion of air, of a slight excess of a chiral phosphine ligand.

Thus, the in situ cationic catalyst system, as displayed in formula (F) is prepared in situ from a stable and readily prepared bisdiene metal complex salt (E), and a commercially available chiral phosphine ligand.

$$[M(Diene)L]^+X^- \quad (F)$$

wherein M, Diene, L, and X are defined above.

The preferred catalyst system for use in the instant invention is a mixture of PROPHOS and [Rh(norbornadiene)$_2$]$^+$PF$_6^-$.

The in situ cationic catalyst system is treated with hydrogen gas at 1 atmosphere prior to the introduction of the substrate (D). In this way a cationic hydrogenation catalyst is formed in situ.

Each component of the novel in situ catalyst system, that is, the cationic bisdiene metal complex, the non-nucleophilic anion and the chiral phosphine ligand may be employed in amounts ranging from 0.5 to 10 percent by weight, preferably 1 to 3 percent by weight, most preferably 2 percent by weight of the component (D).

The preparation of L-phenylalanine compounds (II) by the catalytic reduction of compound (D) may be carried out at ambient conditions at one atmosphere of hydrogen for a period approximately between 3 and 280 hours. Higher pressures and temperatures may be utilized, particularly in an autoclave, with reduction temperature limitations existing between the freezing and boiling points of the solvent which is utilized.

Depending upon the selection of catalyst system and the R, R', R$_1$, and R$_2$ substituents on L-phenylalanine compound (II) the optical purity of the L-phenylalanine derivatives which are recovered from the catalytic reduction of compound (D) may range from 3 to 92% ee. For example, utilizing two percent by weight of both PROPHOS as the chiral phosphine ligand and [Rh(C$_7$H$_8$)$_2$]$^+$PF$_6^-$ as the catalyst system produces a corresponding L-methyl-N-benzoyl-3,4-dimethoxyphenylalanine compound (F) having an optical purity ranging from 72-91% ee or a L-methyl-N-acetyl-3,4-dimethoxyphenylalanine compound (G) having an optical purity ranging from 84-92% ee. Utilizing two percent by weight of both BINAP as the chiral phosphine ligand produces a compound (F) having an optical purity ranging from 28-57% ee or a compound (G) ranging from 3-11% ee.

The L-phenylalanine compounds which are recovered from the catalytic reduction step are conveniently recrystallized in a solvent system such as hexane/methylene chloride, pentane/trichloromethane, methanol or other suitable solvent to produce a recrystallized L-phenylalanine compound (II) such as L-methyl-N-benzoyl-3,4-dimethoxyphenylalanine which has an optical purity in the range of 96-98% ee if it was previously prepared utilizing PROPHOS in the catalyst system. Thus a significant enrichment in optical purity, is achieved by simple recrystallization.

The recrystallized optically purified L-phenylalanine compounds (II) are hydrolyzed with a dilute acid, preferably hydrochloric acid. The hydrolyzed product is an amino acid salt represented by structural formual (III) when hydrolyzed with HCl.

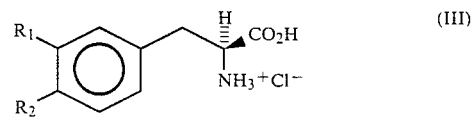

wherein R$_1$ and R$_2$ are defined above.

Other suitable acids include but are not limited to sulfuric, nitric, hydrobromic, acetic, picric or maleic acid. The dilute acid can be utilized in the range of 5-50% by weight, preferably 20% by weight or less than 40% by weight to prevent substituent cleavage. The acid hydrolysis step preferably occurs under reflux conditions. The hydrolysis may proceed at ambient temperature but hydrolysis proceeds at a faster rate at increased temperature and pressure, which would be obvious to one skilled in the art.

The compound of Formula III is treated to undergo a Pictet-Spengler ring closure which is represented by the following scheme:

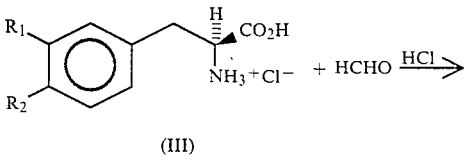

(III)

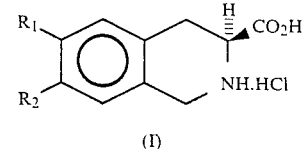

(I)

In this method the amino acid salt compound (III) is subjected to a ring-closure reaction to yield the object chiral L(S)-IQCA compound (I). The ring-closure reaction is carried out by reacting the amino acid salt compound (III) with formaldehyde or a reactive derivative thereof.

The present ring-closure reaction is preferably carried out in the presence of an acid. Suitable acids include, for example, an inorganic acid (e.g., hydrochloric acid, sulfuric acid, nitric or hydrobromic acid) or an organic acid (e.g., acetic acid, propionic acid or picric acid). The reaction is usually carried out with or without solvent at room temperature or under warming or heating. Suitable solvents include, for example, methanol, ethanol, n-butanol, water, benezene, chloroform, dioxane, and the like.

The final recovered product (I) is in optically pure L-(S) form, optimally 94–97% ee depending on the substituents and the catalytic system which is utilized.

The invention is illustrated by the following examples which exemplify the synthesis of optically pure compounds represented by structural Formulas I and II as well as precursor compounds used in their synthesis.

EXAMPLE 1

α-Benzoylamino-β-(3,4-dimethoxyphenyl)-acrylic Acid Azlactone

This compound was prepared in 68% isolated yield from 3,4-dimethoxybenzaldehyde and hippuric acid according to the procedure of Buck and Ide *Organic Synthesis Collective Volume* 2, 1943, J. Wiley & Sons, New York, pps. 55–56. MP 152°–154° C. (lit. 151°–152° C.).

EXAMPLE 2

α-Acetylamino-β-(3,4-dimethoxyphenyl)-acrylic Acid Azlactone

This compound was prepared in 40% isolated yield from 3,4-dimethoxy-benzaldehyde and acetylglycine by a modification of the procedure of Buck and Ide (supra.) MP 168°–172° C. (U.S. Pat. No. 3,882,172 reports an MP of 165°–169° C.).

EXAMPLE 3

Methyl α-Benzoylamino-3,4-dimethoxycinnamate

This compound was prepared in 84% yield from the product of Example 1 by treatment with sodium carbonate in methanol using the procedure of Saxena et al, *Indian J. Chemistry*, (1975), 13, 23. MP 135°–137° C.

EXAMPLE 4

α-Acetylamino-3,4-dimethoxycinnamic acid

A one L single-necked flask was charged with 43.68 g (0.1767 moles) of the azlactone prepared in Example 2, 125 mL of water, and 320 mL of acetone. The reaction mixture was heated under reflux for 17.5 hours, then diluted with 200 mL of water and refluxed for a further 23 hours. The apparatus was then adapted for distillation and the acetone was removed. After adding 300 mL of fresh water the reaction mixture was heated under reflux for a further 2 hours, filtered, and the collected solids washed with 2×50 mL of boiling water. The filtrate was refluxed with 10 g of activated carbon for 15 minutes, then filtered, and the carbon was washed with 2×100 mL of boiling water. The filtrate was allowed to cool to room temperature overnight. The resulting white, voluminous precipitate was collected by filtration and washed with 2×50 mL of iced water. After drying at the pump the product was dried in a vacuum desiccator (yield 18.06 g). A similar re-work of the filtrate yielded a second batch of product (9.75 g). The overall yield of the title compound was 27.81 g (59%); MP 212°–214° C.; $^1$HNMR (d6-DMSO) δ≈12.5 (br, 0.5 H, part. exch.), 9.42 (s, 0.7 H, part. exch.), 7.31 (d, J=1.65 Hz, 1H), 7.23 (s, 1H), 7.20 (dd, J=8.4 and 1.65 Hz, 1H), 6.99 (d, J=8.4 Hz, 1H), 3.79 (s, 3H), 3.76 (s, 3H), 2.0 (s, 3H).

EXAMPLE 5

Methyl α-Acetylamino-3,4-dimethoxycinnamate

This compound was prepared from the product of Example 2 by treatment with sodium carbonate in methanol by a modification of the procedure of Saxena et al (supra). Alternatively, it could be made by esterification of α-acetylamino-3,4-dimethoxycinnamic acid. Thus, 9.62 g of the acid was heated under reflux for 19 hours in 100 mL of methanol containing 1 mL of concentrated hydrochloric acid. After diluting with 500 mL of water, the solution was basified with a 10% aqueous solution of sodium carbonate to a pH of 8–9. The resultant solids were collected by filtration, washed with 3×50 mL of water and dried at the pump. The crude product was further purified by column chromatography on silica gel, eluting with a gradient of methylene chloride/methanol (99:1 thru 96:2). After stripping the solvent from the appropriate fractions, and drying at the pump 2.07 g (21%) of the title compound were obtained; $^1$HNMR (CDCL$_3$) 7.42 (s, 1H), 7.10 (d, J=8.5 Hz, 1H), 7.07 (s, 1H), 6.99 (s, 1H), 6.86 (d, J=8.5 Hz, 1H), 3.91 (s, 3H), 3.86 (s, 3H), 3.84 (s, 3H), 2.17 (s, 3H); MP 198°–200° C. Anal. calcd for $C_{14}H_{17}NO_5$: C, 60.2; H, 6.14; N, 5.02. Found: C, 60.42; H, 5.78; N, 4.53.

EXAMPLE 6

α-Benzoylamino-3,4-dimethoxycinnamic acid

This compound was prepared according to the method of Deuloffeu and Mendivelzua *Z. Physiol. Chem.* (1933), 219, 23 by the hydrolysis of the azlactone product of Example 1 with refluxing 2% aqueous NaOH over 2 hours. The yield was 87%, MP 198°–199.5° C. (Butterick, J. R. and Unrau, A. M., *Can. J. Chem.*, (1974), 52, 2873, report an MP of 196°–198° C.).

EXAMPLE 7

Rhodium (I) bis(norbornadiene) hexafluorophosphate

This preparation was based on the generalized procedure for making cationic rhodium complexes described by Schrock and Osborn, *J. Amer. Chem. Soc.*, (1971), 93, 3089. Thus, a 50 mL round-bottomed flask equipped with a magnetic stirrer was charged under a dry nitrogen atmosphere with rhodium norbornadiene chloride dimer (0.4855 g, 2.11 mmol) and 10 mL of dried, oxygen-free THF. To this was added a solution containing silver hexafluorophosphate (0.5334 g 2.11 mmol) in 10 mL of THF. An immediate precipitate of silver chloride was formed and after stirring for 14 minutes this was collected by filtration in a dry-box, and washed with 2×2 mL of THF. To the dark amber filtrate was added freshly distilled norbornadiene (0.1958 g, 2.13 mmol) in 2 mL of THF, causing the color to turn deep red/-maroon and the gradual formation of a precipitate. The reaction mixture was stirred overnight (16 hours) at room temperature, after which time, the maroon solids were collected by filtration and washed with 4×2 mL of THF. Drying in vacuum (0.2 mmHg) produced analytically pure material as a brick red solid (0.4049 g, 47%): $^1$HNMR (CD$_2$Cl$_2$) 5.65 (dd, J=2.1 and 4.7 Hz, 4H), 4.82 (br s, 2H), 1.66 (t, J=1.5 Hz, 2H); $^{31}$PNMR (CD$_2$Cl$_2$) −143.83 (sp, J=711 Hz). Anal. calcd for $C_{14}H_{16}RhPF_6$: C, 38.91; H, 3.73. Found: C, 38.56; H, 3.63.

EXAMPLE 8

Preparation of L-Methyl
N-Benzoyl-3,4-dimethoxyphenylalanine by the
Asymmetric Hydrogenation of Methyl
-Benzoylamino-3,4-dimethoxycinnamate Into a dry 500 mL round-bottomed 3-necked flask equipped with a magnetic stirrer, a reflux condenser, 2 three-way stopcocks attached to rubber balloons (Aldrich Chemical Company), a septum, and a nitrogen manifold, was injected a solution containing rhodium (I) bis(norbornadiene) hexafluorophosphate (0.2579 g), 59.7 μmol, 2.6 wt %, 0.2 mole %) in dry THF (10 mL). A further 10 mL of THF was used to ensure a complete transfer. To the bright orange/red was then injected a solution of R-PROPHOS (0.2499 g. 60.6 μmol, 2.5 wt %, 0.2 mole %) in 5 mL of dry THF. Two 5 mL rinses with THF were used to complete the transfer. The addition caused an immediate color change to a bright orange/yellow. After stirring at room temperature for 15 minutes the flask was evacuated using a water aspirator and purged with hydrogen (via the balloons). This process was repeated four more times. The reaction mixture was then stirred under a hydrogen atmosphere at room temperature for 30 minutes after which time the color had changed to a dull organge/amber brown. At this time a solution of the title compound of Example 2 (9.9998 g, 29.3 mmol) in dry THF (80 mL) was injected via the septum. Two 15 mL rinses were used to ensure a complete transfer. The addition caused the color to take on a bright deep red hue, and upon letting the mixture stir for 1 hour this became a ruby red. The reaction mixture was stirred overnight (16 hours) after which time the dull orange/amber brown color had returned and the reaction was quenched by purging with nitrogen gas. Cleaned Dowex ® 50×2-400 ($\approx$10 g) was then added and stirring was continued for 1 hour. The reaction mixture was then added to the top of a silica column and the product was eluted with THF. After drying over anhydrous sodium sulfate the solvent was removed on a rotary evaporator to yield an oil. This oil was pumped at 0.02–0.05 mmHg overnight (16 hours) to afford the crude product as a cream/light yellow solid (11.64 g, 89.9 ee % of L-isomer by LC).

Product Enrichment

The product was enriched by recrystallization from methylene chloride/hexane and the mother liquor was stripped and re-worked to yield in total 3 batches of pure L-methyl N-benzoyl-3,4-dimethoxyphenylalanine (5.69 g, 1.25 g, and 1.90 g, total=8.84 g, 25.7 mmol, 87.7%. 95.9–97.7 ee% of L-isomer by LC. MP 124°–125° C., 125.5°–126.5° C. $[\alpha]_D 23$ (c 2.4, CHCl$_3$)=+83°–86°. (Selke, S. and Pracejus, H., *DD East German Patent,* (1980), 140036; report an optical rotation of +55.8°–76.6°). The final residue from the mother liquor was found to consist of almost completely racemic material (0.59 g, 1.72 mmol, 5.9%, 1.7 ee% of L-isomer by LC. MP 105°–107° C.).

EXAMPLE 9

Preparation of
L-N-Acetyl-3,4-dimethoxyphenylalanine

Using the procedure of Example 8 the title compound was prepared in 98% yield and 91.6% ee from α-acetylamino-3,4-dimethoxycinnamic acid after 1.5 hours.

EXAMPLE 10

Preparation of
L-N-Benzoyl-3,4-dimethoxyphenylalanine

Using the procedure of Example 8 the title compound was prepared in 100% yield and 90.9% ee from α-benzoylamino-3,4-dimethoxycinnamate after 5.5 hours.

EXAMPLE 11

Preparation of L-Methyl
N-Acetyl-3,4-dimethoxyphenylalanine

Using the procedure of Example 8 and using methanol as the solvent the title compound was prepared in 100% yield and 84.3% ee from methyl α-acetylamino-3,4-dimethoxycinnamate after 6.5 hours.

EXAMPLE 12

Preparation of L-Methyl
N-Benzoyl-3,4-dimethoxyphenylalanine

Using the procedure of Example 8 and using methanol as the solvent the title compound was prepared in 99.3% yield and 85.1% ee from methyl α-benzoylamino-3,4-dimethoxycinnamate after 2 hours.

EXAMPLE 13

Preparation of
L-N-Benzoyl-3,4-dimethoxyphenylalanine

Using the procedure of Example 8 and using methanol as the solvent the title compound was prepared in 84.0% yield and 72.1% ee from α-benzoylamino-3,4-dimethoxycinnamic acid after 136 hours.

EXAMPLE 14

Preparation of
L-N-Acetyl-3,4-dimethoxyphenylalanine

Using the procedure of Example 8 and using methanol as the solvent the title compound was prepared in 100% yield and 88.6% ee from methyl α-acetylamino-3,4-dimethoxycinnamic acid after 3.4 hours.

EXAMPLE 15

Preparation Of
L-N-Acetyl-3,4-dimethoxyphenylalanine

Using the procedure of Example 8 and using R-BINAP as the catalyst the title compound was prepared in approximately 70% yield and 3.1% ee from α-acetylamino-3,4-dimethoxycinnamic acid after 243 hours.

EXAMPLE 16

Preparation of
L-N-Benzoyl-3,4-dimethoxyphenylalanine

Using the procedure of Example 8 and using R-BINAP as the catalyst the title compound was prepared in 100% yield and 50.2% ee from α-benzoylamino-3,4-dimethoxycinnamic acid after 5.5 hours.

EXAMPLE 17

Preparation of L-Methyl
N-Acetyl-3,4-dimethoxyphenylalanine

Using the procedure of Example 8 and using R-BINAP as the catalyst the title compound was prepared in 36% yield and 10.5% ee from methyl α-acetylamino-3,4-dimethoxycinnamate after 279 hours.

EXAMPLE 18

Preparation of L-Methyl N-Benzoyl-3,4-dimethoxyphenylalanine

Using the procedure of Example 8 and using R-BINAP as the catalyst the title compound was prepared in 99.2% yield and 57.3% ee from methyl α-benzoylamino-3,4-dimethoxycinnamate after 5 hours.

EXAMPLE 19

Preparation of L-Methyl N-Acetyl-3,4-dimethoxyphenylalanine

Using the procedure of Example 8 and using R-BINAP as the catalyst and methanol as the solvent the title compound was prepared in 76% yield and 6.5% ee from methyl α-acetylamino-3,4-dimethoxycinnamate after 150 hours.

EXAMPLE 20

Preparation of L-N-Benzoyl-3,4-dimethoxyphenylalanine

Using the procedure of Example 8 and using R-BINAP as the catalyst and methanol as the solvent the title compound was prepared in 64.0% yield and 27.9% ee from α-benzoylamino-3,4-dimethoxycinnamic acid after 136 hours.

EXAMPLE 21

Preparation of L-N-Acetyl-3,4-dimethoxyphenylalanine

Using the procedure of Example 8 and using R-BINAP as the catalyst and methanol as the solvent the title compound was prepared in 96.6% yield and 10.8% ee from methyl α-acetylamino-3,4-dimethoxycinnamic acid after 3.4 hours.

EXAMPLE 22

(Comparative)

Preparation of Racemic Methyl N-Benzoyl-3,4-dimethoxyphenylalanine

Methyl α-benzoylamino-3,4-dimethoxycinnamate (20 g) was treated with 10% palladium on carbon (2 g) in methanol (400 mL) under a hydrogen atmosphere (1 atm.) for 3 days. The reaction mixture was then filtered and the solvent stripped to yield the title compound (18.90 g, 95%); MP 106°–107° C.

EXAMPLE 23

Preparation of L-3,4-Dimethoxyphenylalanine Hydrochloride

The procedure was based on that used by Saxena et al (supra.) for the hydrolysis of the racemic material. Thus a 2 L round-bottomed, 3-necked flask was charged with 12.01 g (35.2 mmol) of L-methyl N-benzoyl-3,4-dimethoxyphenylalanine (98.8% ee) as prepared in Example 8, 1.08 L of water, and 276 mL of concentrated hydrochloric acid. The reaction mixture was heated under reflux for 20 h and then allowed to cool to room temperature. It was then filtered and the collected solids were washed with 2×25 mL of water. The filtrate was then extracted with 5×200 mL of methylene chloride. The aqueous layer was stripped on a rotary evaporator, and the residue was dried at the pump to yield the title product (8.73 g 94.8%); MP 218°–219° C. (Yamato, H. and Hayakawa, T., *Polymer*, (1978), 19, 963, report an MP of 220° C.); ¹HNMR (d6-DMSO) 8.52 (s, 3H, exch. D₂O), 6.98 (d, J=1.5 Hz, 1H), 6.89 (d, J=8.2 Hz, 1H), 6.78 (dd, J=8.2 and 1.5 Hz, 1H), 4.11 (m, 1H), 3.75 (s, 3H), 3.73 (s, 3H), 3.11 (m, 2H); IR (KBr) 3612–3343 m, 3290–2400 s, 1740 m, 1608 m, 1517 s, 1250 s, 1144 m, 1022 m cm⁻¹.

EXAMPLE 24

(Comparative)

Preparation of Racemic 3,4-Dimethoxyphenylalanine Hydrochloride

Using the procedure of Example 23 racemic methyl N-benzoyl-3,4-dimethoxyphenylalanine was hydrolyzed to the title compound in 93% yield.

EXAMPLE 25

Preparation of 6,7-Dimethoxy-1,2,3,4-tetrahydroisoquinoline-3(S)-Carboxylic Acid The procedure was based on that used by Dean and Rapoport, *J. Org. Chem.* (1978), 43, 2115, and also Saxena et al (supra.) for the racemic system. Thus, a 50 mL, round-bottomed, single-necked flask was charged with 7.00 g (26.9 mmol) of L-3,4-dimethoxyphenylalanine hydrochloride, 5 mL of concentrated hydrochloric acid, 95 mL of water, and 4.2 mL of 37% aqueous formaldehyde solution. The reaction mixture was heated with a bath temperature of 90° C for 3 hours under a nitrogen atmosphere. It was then allowed to cool to room temperature and stored in a refrigerator ($\approx 0°$ C.) overnight (16 hours). To further precipitate product the flask was cooled in a freezer until ice formation had just begun. The cream-colored precipitate was then collected by filtration and washed with 2×5 mL of iced water. After sucking dry the product was further dried in a vacuum desiccator over phosphorus pentoxide to yield 6.26 g (85%) of the title compound as a cream colored powder; MP 278°–279° C. dec (Klutchko, S. et al, *J. Med. Chem.*, (1986), 29, 1953, report an MP of 281°–282° C. dec.); $[\alpha]_D^{35} -92.1°$, (c 2.45, 1N HCl, (Klutchko, S. et al) $[\alpha]_D^{23} -98$, (c 2.5, 1N HCl) ; 94.0% ee; ¹HNMR (CF₃COOD) 9.06 (acid peak), 6.90 (s, 1H), 6.83 (s, 1H), 4.64 (AB, J=15.8 Hz, 1H), 4.60 (AB, J=15.8 Hz, 1H), 4.57 (dd, J=10.0 and 5.5 Hz, 1H), 3.96 (s, 3H), 3.94 (s, 3H), 3.57 (dd, J=17.0 and 5.5 Hz, 1H), 3.44 (dd, J=17.0 and 10.0 Hz, 1H); IR (KBr) 3561–3304 s, 3256–2367 s, 1734 s, 1522 s, 1267 s, 1224 s, 1121 s cm⁻¹. Recrystallization from hot 0.1N aqueous hydrochloride acid afforded an analytical sample (recovery 72%, MP 279°–280° C. dec). Anal. calcd for C₁₃H₁₆ClNO₄: C, 52.66; H, 5.89; N, 5.12. Found: C, 52.63; H, 5.63; N, 5.12.

EXAMPLE 26

(Comparative)

Preparation of Racemic 6,7-Dimethoxy-1,2,3,4-tetrahydroisoquinoline-3-carboxylic Acid Using the procedure in Example 25 racemic 3,4-dimethoxyphenylalanine hydrochloric was cyclized to the title compound in quantitative yield (MP 273°–275° C.).

What is claimed is:

1. A method of producing an optically pure compound comprising L(S)-1,2,3,4-tetrahydroisoquinoline-3-carboxylic acid represented by the formula:

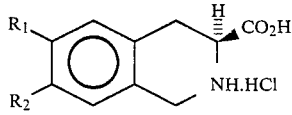

wherein $R_1$ and $R_2$ are independently hydrogen, lower alkyl, lower alkoxy, lower alkylthio, lower alkylsulfinyl, lower alkylsulfonyl, hydroxy or $R_1$ and $R_2$ together are methylenedioxy, comprising:

(a) hydrogenating, in the presence of an in situ cationic catalyst comprising:
  (1) a chiral phosphine ligand; and
  (2) $[M(Diene)_2]^+X^-$ wherein M is selected from the group consisting of Rh, Ru, Pt, Pd, and Ni, Diene is norbornadiene or cyclooctadiene, and $X^-$ is selected from the group consisting of $PF_6^-$, $ClO_4^-$, and $BF_4^-$; a primary precursor compound represented by the formula:

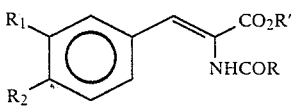

to produce a hydrogenated compound represented by the formula:

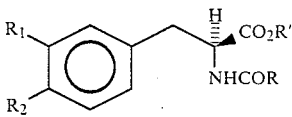

wherein R' is H or $CH_3$ and R is $C_6H_5$ or $CH_3$;
(b) hydrolyzing the hydrogenated compound to produce an optically pure amino acid salt; and
(c) performing a Pictet-Spengler ring closure of the amino acid salt to yield the optically pure L(S)-1,2,3,4-tetrahydroisoquinoline-3-carboxylic acid compound.

2. The method of claim 1 wherein the chiral phosphine ligand is (R)—(+)—2,2'-bis(diphenylphosphino)-1,1'-binaphthyl.

3. The method of claim 1 wherein the chiral phosphine ligand is (R)—(+)—1,2-bis(diphenylphosphino)-propane.

4. The method of claim 1 wherein the catalyst component (b) is $[Rh(C_7H_8)_2]^+X^-$.

5. The method of claim 4 wherein $X^-$ is $PF_6^-$.

6. The method of claim 1 wherein the chiral phosphine ligand is selected from the group consisting of CHIRAPHOS, DIPAMP, NORPHOS, DIOP, CAMPHOS and DIOXOP.

7. The method of claim 1 wherein catalyst component (a) is ((R)—(+)—1,2-bis(diphenylphosphino)propane and catalyst component (b) is $[Rh(C_7H_8)_2]^+PF_6^-$.

8. Optically pure compound L(S)-6,7-dimethoxy-1,2,3,4-tetrahydroisoquinoline-3-carboxylic acid is prepared according to the method of claim 1.

9. A method of producing an optically pure L-phenylalanine compound represented by the formula comprising:

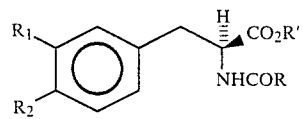

by hydrogenating, in the presence of an in situ cationic catalyst comprising:
(a) a chiral phosphine ligand; and
(b) $[M(Diene)_2]^+X^-$ wherein M is selected from the group consisting of Rh, Ru, Pt, Pd and Ni Diene is norbornadiene or cyclooctadine, $X^-$ is selected from the group consisting of $PF_6^-$, $ClO_4^-$, and $BF_4^-$; a precursor compound represented by the formula:

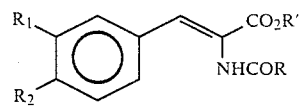

wherein $R_1$ and $R_2$ are independently hydrogen, lower alkyl, lower alkoxy, lower alkylthio, lower alkylsulfinyl, lower alkylsulfonyl, hydroxy or $R_1$ and $R_2$ together are methylenedioxy, R' is H or $CH_3$ and R is $C_6H_5$ or $CH_3$.

10. The method of claim 9 wherein the chiral phosphine ligand is (R)—(+)—2,2'-bis(diphenylphosphino)-1,1'-binaphthyl.

11. The method of claim 9 wherein the chiral phosphine ligand is (R)—(+)—1,2-bis(diphenylphosphino)-propane.

12. The method of claim 9 wherein the chiral phosphine ligand is selected from the group consisting of CHIRAPHOS, DIPAMP, NORPHOS, DIOP, CAMPHOS and DIOXOP.

13. The method of claim 11 wherein the catalyst component (b) is $[Rh(C_7H_8)_2]^+PF_6^-$.

14. The method of claim 9 wherein the L-phenylalanine compound is selected from the group consisting of L-N-acetyl-3,4-dimethoxyphenylalanine, L-methyl-N-acetyl-3,4-dimethoxyphenylalanine, L-N-benzoyl-3,4-dimethoxyphenylalanine and L-methyl-N-benzoyl-3,4dimethoxyphenylalanine.

15. The method of claim 14 wherein the L-phenylalanine compound produced is enriched by recrystallization.

* * * * *